United States Patent
Young et al.

(10) Patent No.: US 7,625,348 B2
(45) Date of Patent: Dec. 1, 2009

(54) ORTHOTIC LINER

(75) Inventors: Peter Marshall Young, Plymouth, MN (US); Kelly B. Clark, Coon Rapids, MN (US); Karin E. Pauly, Becker, MN (US); William M. Clover, Jr., Buffalo, MN (US)

(73) Assignee: Otto Bock HealthCare LP, Minneapolis, MN (US)

( * ) Notice: Subject to any disclaimer, the term of this patent is extended or adjusted under 35 U.S.C. 154(b) by 283 days.

(21) Appl. No.: 11/426,073

(22) Filed: Jun. 23, 2006

(65) Prior Publication Data
US 2006/0293621 A1  Dec. 28, 2006

Related U.S. Application Data

(60) Provisional application No. 60/694,122, filed on Jun. 24, 2005.

(51) Int. Cl.
*A61F 13/00* (2006.01)
(52) U.S. Cl. .................. 602/5; 602/27; 602/60; 602/61; 602/62
(58) Field of Classification Search .......... 602/5, 602/20, 23, 27
See application file for complete search history.

(56) References Cited

U.S. PATENT DOCUMENTS

| | | | |
|---|---|---|---|
| 3,955,565 A * | 5/1976 | Johnson, Jr. ............ | 602/12 |
| 4,454,871 A | 6/1984 | Mann et al. | |
| 4,628,945 A * | 12/1986 | Johnson, Jr. ............ | 602/27 |
| 5,226,875 A | 7/1993 | Johnson | |
| 5,372,576 A | 12/1994 | Hicks | |
| 5,571,206 A | 11/1996 | Varn | |
| 5,948,707 A * | 9/1999 | Crawley et al. ............ | 442/101 |
| 6,120,471 A | 9/2000 | Varn | |
| 6,860,864 B2 | 3/2005 | Meyer | |
| 2006/0084899 A1* | 4/2006 | Verkade et al. ............ | 602/27 |

OTHER PUBLICATIONS

Printout from website, "Foot Orthoses-MPO 2000 with Transfer Attachment," http://www.rcai.com, 1 pg, printed May 5, 2005.
Printout from website, "Foot Orthoses-Multi Podus, Burn Unit MPO," http://www.rcai.com, 1 pg, printed May 5, 2005.
American Orthotic & Prosthetic Association, "Code, Descriptor, Graphic AOPA Interpretation," p. 138, 2005.

* cited by examiner

*Primary Examiner*—Kim M Lewis
(74) *Attorney, Agent, or Firm*—Faegre & Benson, LLP

(57) ABSTRACT

An orthotic device includes a rigid support member and a removable inner liner having a contact surface adjacent the support member formed of a non-skid or non-slip material. The liner may include a flap or pocket for receiving at least a portion of the support member, at least at first strap having a first end attached to a first region of the liner and a second end fastenable to a second region of the liner for securing the orthotic device to the wearer, and a patient interface surface.

10 Claims, 7 Drawing Sheets

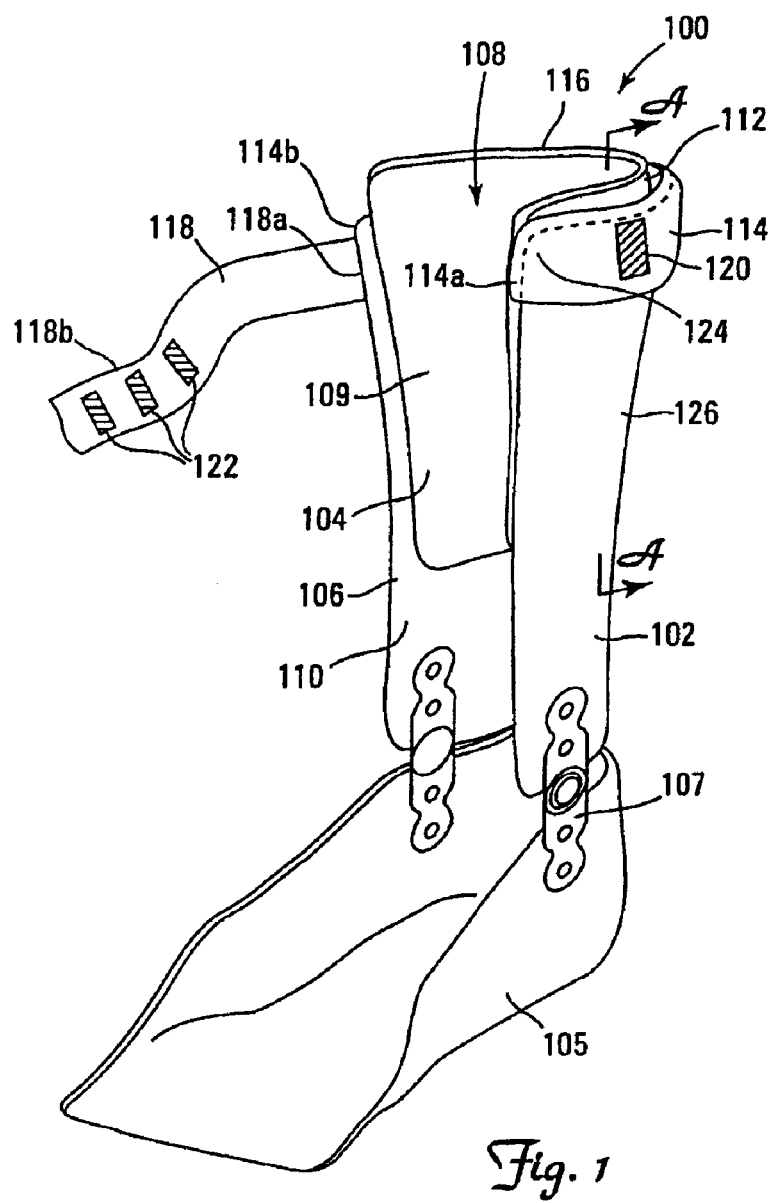
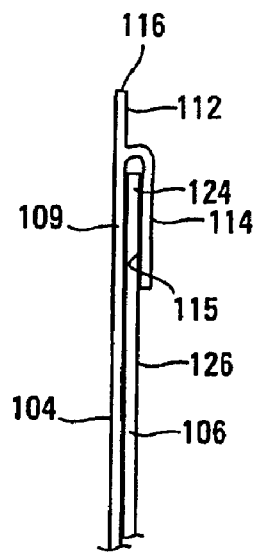
Fig. 1
Fig. 3

ORTHOTIC LINER

RELATED APPLICATIONS

This application claims the benefit of Provisional U.S. Pat. Appln. Ser. No. 60/694,122 entitled "Orthotic Liner" filed on Jun. 24, 2005, the entire disclosure of which is hereby incorporated herein by reference.

TECHNICAL FIELD

The present invention relates to orthotic devices for stabilizing a part of the body. More specifically, the invention relates to an integrated liner and strap for use with an orthotic device.

BACKGROUND

Traditional orthotic devices are worn to support, stabilize or position a particular part of the body. Orthotic devices for stabilizing the hand, wrist, upper and lower arms, foot, ankle, upper and lower legs, torso and neck are known in the art. Unlike casts, orthotic devices are donned and removed by the user and may be worn throughout the day, only during specific activities, or when the user feels it necessary.

Orthotic devices typically include a rigid or semi-rigid support or splint member and a padded or cushioning inner liner. Orthotic liners may be secured to the support member by adhering the liner to the inside of the support member, sometimes during a thermoforming process. However, a liner permanently affixed to the support member is difficult to clean.

Finally, orthotic devices typically include a strap or other means of securing the orthotic to the body. Orthotic strapping has been accomplished with the use of a hook and loop strap riveted to the support member. The strap is then fed through a plastic chafe with a D-ring riveted through the opposing side of the support member. The strap is secured with sufficient tension to retain the orthotic device in position. Unfortunately, such strapping has many drawbacks. The strap tends to become dirty easily and the hook portion particularly tends to collect debris. But, because the strap is permanently fixed to the support member, it is very difficult to clean. Furthermore, after repeated use, the napping loop of the hook and loop material often loses shear strength. Finally, the hardware associated with the strapping adds weight to the orthotic and can chafe the wearer.

There is a need, therefore, for an orthotic device having an improved liner and means of securing to the wearer's body.

SUMMARY

In one embodiment, the present invention is an orthotic liner for an orthotic device for supporting a portion of the body. The orthotic liner includes a body member sized and shaped to conform to at least a portion of a support member inner surface. The body member further has a non-slip outer surface adjacent the support member inner surface. The liner is fixed in position relative to the support member upon contact between the body member outer surface and the support member inner surface.

In another embodiment, the present invention is an orthotic device including a support member and a liner. The support member is sized and shaped to support a portion of the body, and has an inner surface for receiving the portion of the body. The liner is sized and shaped to conform to at least a portion of the support member inner surface. The liner further includes a non-slip outer surface adjacent the support member inner surface. The liner is fixed in position relative to the support member upon contact between the body member outer surface and the support member inner surface.

In yet another embodiment, the present invention an orthotic device for supporting a portion of the body. The orthotic device includes a support member including a foot support hingedly coupled to a calf support. The support member has an inner surface for receiving the portion of the body. The orthotic device further includes a liner sized and shaped to conform to at least a portion of the support member inner surface. The liner has a non-slip outer surface adjacent the support member inner surface. The liner is fixed in position relative to the support member upon contact between the liner outer surface and the support member inner surface.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 shows an orthotic device according to one embodiment of the present invention.

FIG. 3 shows a cross-sectional view taken along line A-A of a portion of the orthotic device of FIG. 1.

Figure 2:
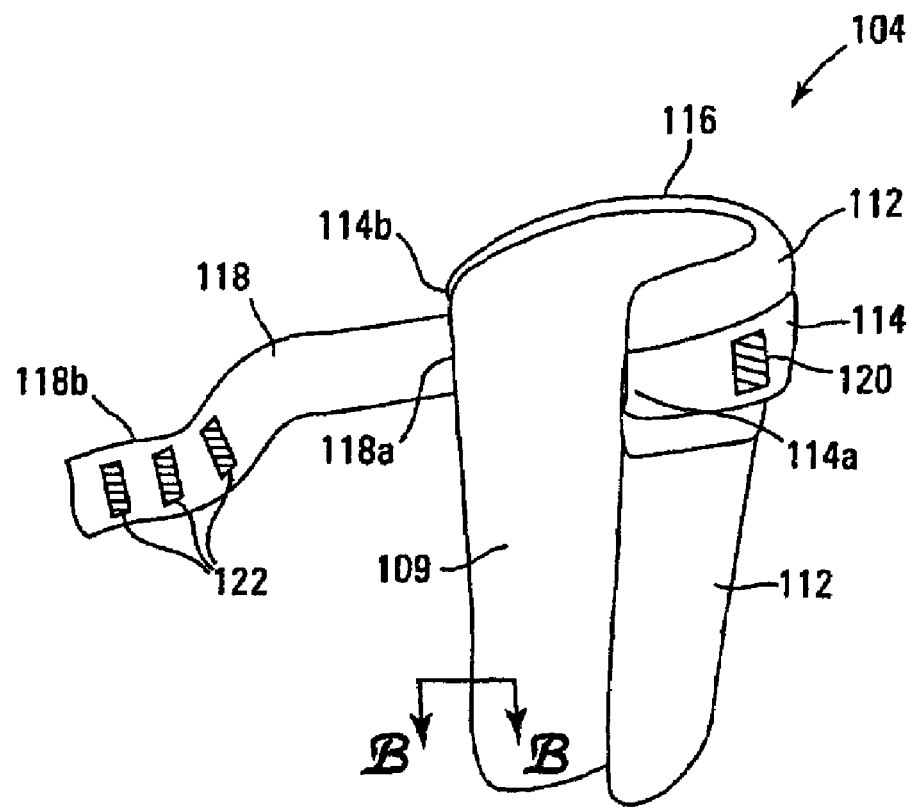
FIG. 2 shows the liner of FIG. 1.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a lower-leg orthotic device 100 including a rigid support member 102 and a liner 104 according to one embodiment of the present invention. The support member 102 includes a foot support 105 connected to a calf support 106 at hinge 107. The support member 102 is sized and shaped for supporting the foot and ankle as is known in the art of orthotics. An anterior portion of the support member 102 is open at a gap 108 to facilitate donning and doffing. The liner 104 is completely removable from the support member 102 and can be easily washed or replaced.

The liner 104, as is shown in FIGS. 1 and 2, includes a body member 109 sized and shaped to conform to an inner surface 110 of the support member 102. An outer or contact surface 112 of the liner 104 adjacent the inner surface 110 of the support member is formed of a non-skid or non-slip material. The material of the outer surface 112 is chosen to grip and/or substantially prevent sliding movement between the inner surface 110 of the support member 102 and the outer surface 112 of the liner 104.

The liner 104 may further include a pocket or flap 114 formed on the outer surface 112 of the body member 109. In the present embodiment, the flap 114 extends about a circumference of the body member 109 and is positioned slightly below an upper edge 116 of the body member 109. The flap 114 may be formed integrally with the body member 109, as shown in FIG. 3, or may be secured to the body member 109 as with stitching, adhesive, hook and loop members (i.e., Velcro®), or other suitable means. Each end 114a, 114b of the flap 114 is secured to the body member 109 by stitching, bonding, adhering or by other suitable means. It should be noted that the outer surface 112 of the liner 104 includes an inner surface 115 of the flap 114 as is shown in FIGS. 1-3.

The liner 104 may further include at least one strap 118. A first end 118a of the strap 118 is secured to the liner 104. The first end 118a may be formed integrally with the liner 104, or may be attached to the liner 104 as with stitching, adhesive, hook and loop members (i.e., Velcro®), etc. In the present embodiment, as is shown in FIG. 2, the first end 118a of the strap 118 is secured to the liner 104 at the flap 114. A second end 118b of the strap 118 is fastenable to a second region of the liner 104. In the present embodiment, the strap 118 has a length sufficient to extend over the gap 108 and to overlap at least a portion of the body member 109 opposite the gap 108. The strap 118 and flap 114 are provided with complementary hook and loop members 120 and 122 for fastening to one another. Optionally, the strap 118 is provided with a plurality of hook or loop members 122 spaced apart from one another that may be trimmed off to fit the length of the strap 118 to a particular user. Alternately, the second end 118b of the strap 118 is fastenable to the liner 104 with other means, including hooks, laces, buttons, snaps, or other suitable fasteners.

To don the orthotic device 100, the wearer first places the liner 104 inside of the support member 102 as is shown in FIG. 1. An upper edge 124 of the support member 102 is inserted between the flap 114 and the body member 109, as is shown in FIG. 3. Once the liner 102 is in its desired location, the patient simply inserts the affected limb, in this case the lower leg, into the orthotic device 100 through the gap 106. When donning the orthotic device 100 for the first time, the second end of the strap 118 is trimmed to an appropriate length for the size of the user's limb and any excess hook and loop members 122 are removed. The strap 118 is drawn over the gap 106, tensioned to cause the orthotic device 100 to snugly fit the user's lower leg and secured to the complementary hook and loop member 120 on the liner 104.

The inserted limb causes all or a substantial portion of the outer surface 112 of the liner 104 to contact and grip the inner surface 110 of the support member 102. The inner surface 115 of the flap 114 also grips an outer surface 126 of the support member 102, and is retained in contact by the tensioned strap 118. The non-skid or non-slip outer surface 112 of the liner 104 prevents movement or migration of the support member 102 with respect to the liner 104. The wearer's lower leg, however, is movable relative to the liner 104 within the confines of the strap 118. Thus, during ambulation, shear forces are exerted between the liner 104 and the support member 102, rather than between the wearer's lower leg and the liner 104.

Figure 4:
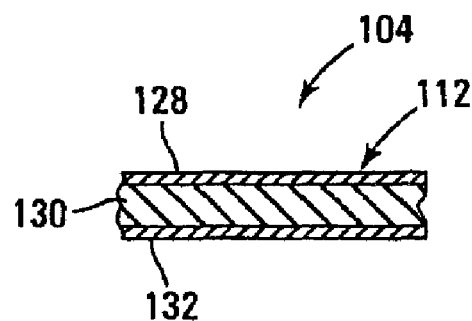
FIG. 4 shows a cross-sectional view of the liner of FIG. 2 taken along line B-B.

FIG. 4 shows the liner 104 in greater detail. The outer surface 112 of the liner 104 may be formed of a variety of materials that are considered non-slip or non-skid. In one embodiment, the outer surface 112 of the liner 104 is formed of Slip-Not®, a resilient, polyvinyl chloride-coated material that is waterproof, washable and resists cracking at temperatures as low as approximately −40° F. (available from Eastex Products, Inc., of Holbrook, Mass.). In other embodiments, the outer surface 112 of the liner 104 is formed of other similar non-skid or non-slip type materials, including silicon. Such materials include non-skid or non-slip materials as are known in the fields of non-skid or non-slip flooring materials. These materials may be provided over the entire outer surface 112 or as beading, cuffs or strips forming an irregular surface texture.

In one embodiment, the liner 104 is laminated or otherwise formed onto an outer surface 128 of an interface 130. In one embodiment, the interface 130 is formed of a cushioning layer material such as foam chosen to improve patient comfort. For example, the interface 130 may be formed of a material that is breathable, wicks moisture away from the skin's surface or is anti-microbial. In one embodiment, the interface 130 is formed of or includes a material that is temperature regulating, such as a microencapsulated phase change material (such as that available from Outlast Technologies, Inc., of Boulder, Colo.).

An inner or patient interface surface 132 of the liner 104 or the interface 130, if there is an interface 130, may be formed of materials that are breathable, can wick moisture away from the skin's surface or are anti-microbial. The patient interface surface 132 may be adapted for contacting the wearer's skin or outer clothing or to facilitate patient comfort. In one embodiment, the patient interface surface 132 is formed of spandex.

A liner 104 in accordance with the present invention may be sized and shaped to be used with virtually any type of orthotic support member as is known in the art. For example, the liner 104 may be used with, but is not limited to, an orthotic for the foot, ankle, lower leg, knee, upper leg, wrist, lower arm, upper arm, torso, head and neck. The following figures show liners and complementary orthotic devices according to a variety of configurations including the features previously described. Each of the embodiments below are intended to incorporate one or more of the features previously described, including flaps or pockets for receiving a support member, straps for securing the liner or orthotic device to the wearer, size adjustability, patient interface surfaces and liner configuration.

Figure 5:
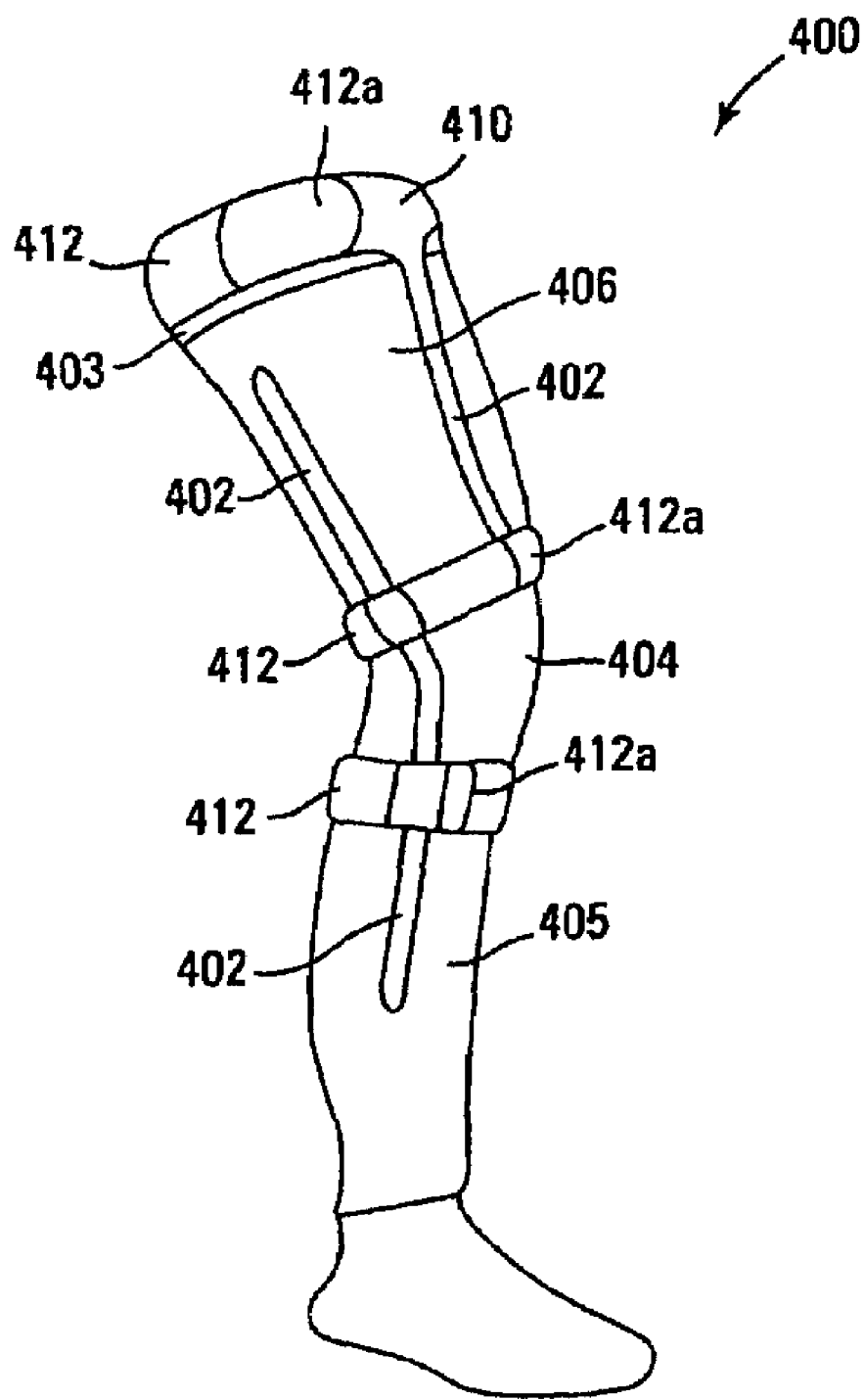
FIG. 5 shows a perspective view of a full leg orthotic device including a liner according to a second embodiment of the present invention.

FIG. 5 shows an orthotic device 400 according to a second embodiment of the present invention. The orthotic device 400 is adapted to be worn over the thigh and calf to stabilize the knee and includes a plurality of movably connected longitudinal support members 402 extending from the thigh to the calf. An upper support member 403 encircles at least a portion of the thigh. The orthotic device 400 further includes a liner 404 having a non-slip or non-skid outer or contact surface 405. The liner 404 is sized and shaped to be worn over the thigh and calf.

The liner 404 includes a generally tubular body member 406 having an upper flap 410 for receiving the upper support member 403. The liner 404 also includes a plurality of straps 412 having a first end formed with or secured to the body member (not shown) and a second end 412a having means for attaching to the liner 404. In the present embodiment, the liner 404 has three straps 412, at upper, lower and middle regions, respectively, of the body member 406 to retain the support members 402 in position.

Optionally, the liner 404 includes an opening at the knee to facilitate patient movement or is separated into an upper liner for the thigh and a lower liner for the calf.

Figure 6:
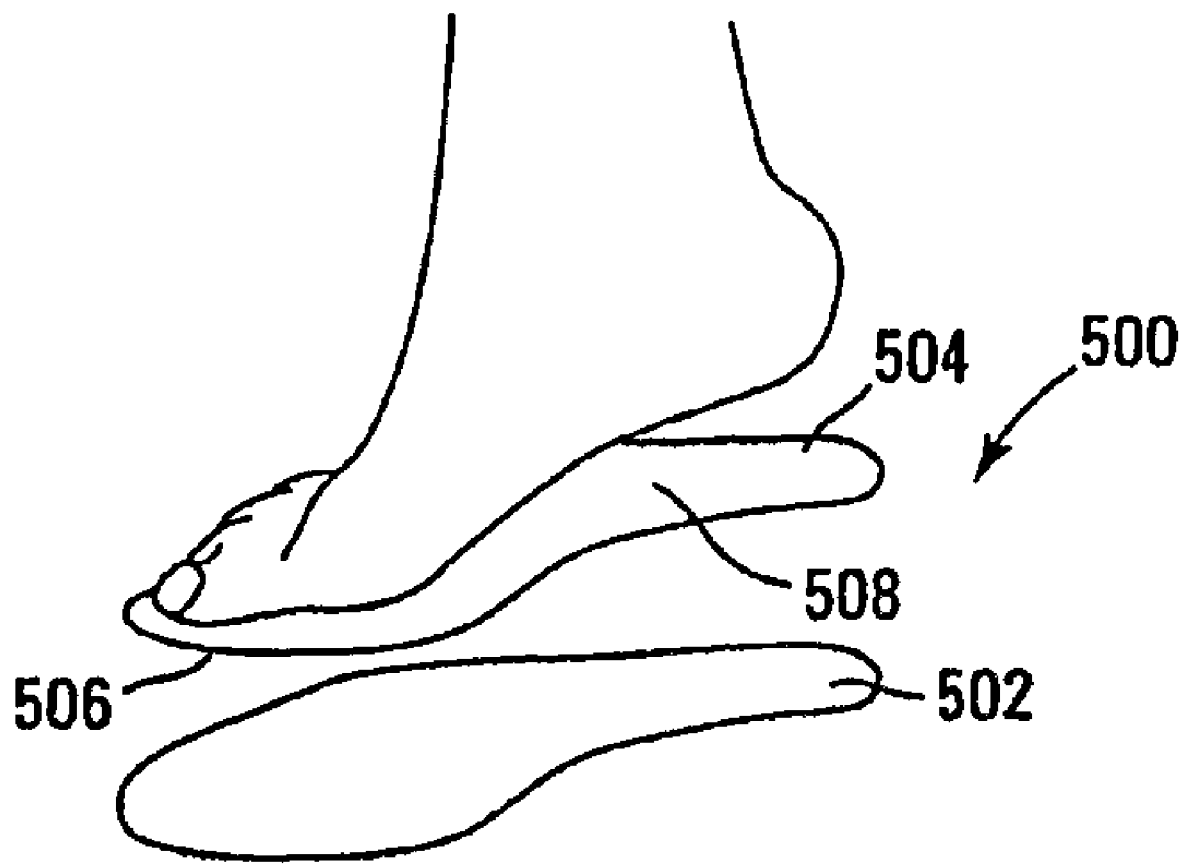
FIG. 6 shows a perspective view of a foot orthotic device including a liner according to a third embodiment of the present invention.

FIG. 6 shows an orthotic device 500 according to a third embodiment of the present invention. The orthotic device 500 includes a support member 502 sized and shaped to be worn as a shoe insert for supporting, for example, the arch of the foot. The orthotic device 500 further includes a liner 504 positioned above the support member 502 adjacent the wearer's foot. A lower or contact surface 506 of the liner 504 adjacent the support member 502 is formed of a non-slip or non-skid material as previously discussed. The liner 504 may be formed on an interface formed of a cushioning material as previously described and may have an inner surface 508 adapted to promote patient comfort.

Figure 7:
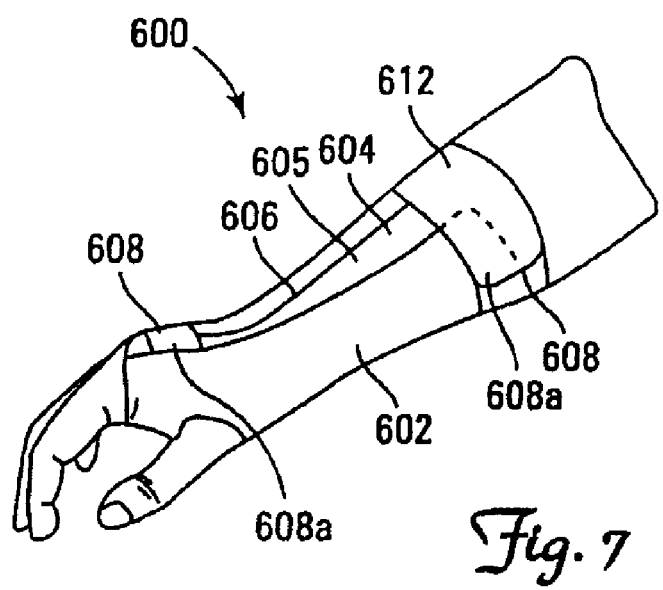
FIG. 7 shows a perspective view of a wrist orthotic device including a liner according to a fourth embodiment of the present invention.

FIG. 7 shows an orthotic device 600 according to a fourth embodiment of the present invention. The orthotic device 600 is adapted to be worn over the lower arm to support the wrist. The orthotic device 600 includes a support member 602 and a liner 604 having a non-slip or non-skid outer or contact surface 605 adjacent the support member 602. The liner 604 includes a body member 606 and a pair of straps 608. A first end of each strap 608 is integral to or attached to the body member 606 (not shown) and a second end 608a of each strap 608 has means for attaching to the body member 606. An upper edge of the body member 606 is formed with a flap 612 for receiving a portion of the support member 602.

In the present embodiment, the liner 604 is donned and the support member 602 is positioned over the liner 604 and inserted under the flap 612. The straps 608 are drawn over the support member 602, tensioned and secured to the body member 606 to secure the orthotic device 600 in place. Alternately, if the support member 602 is configured to encircle the arm or wrist or has considerable surface area, the liner 604 is inserted into the support member 602 first and then the liner 604 and support member 602 are donned and secured to the arm.

Figure 8:
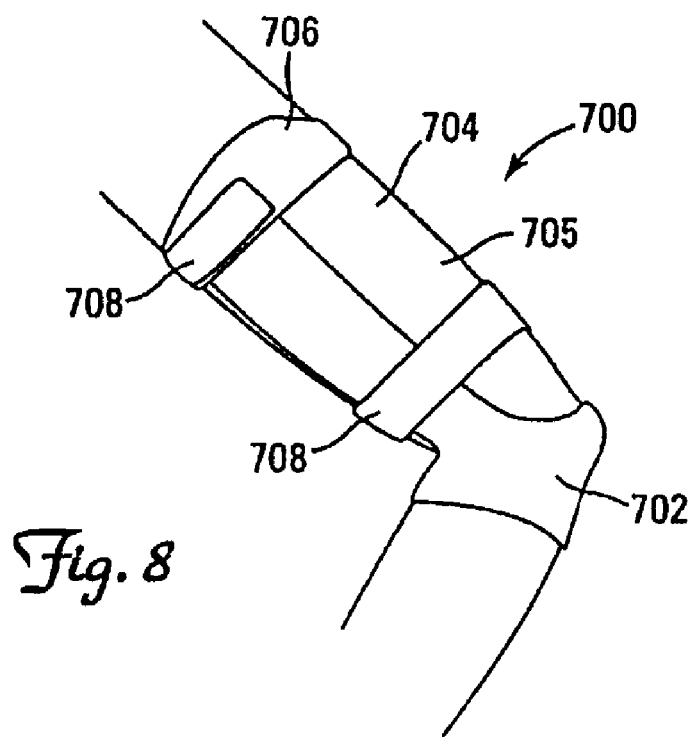
FIG. 8 shows a perspective view of an elbow orthotic device including a liner according to a fifth embodiment of the present invention.

FIG. 8 shows an orthotic device 700 according to a fifth embodiment of the present invention. The orthotic device 700 includes a support member 702 sized and shaped to support and stabilize the lower arm or elbow and a liner 704 having a non-slip or non-skid outer or contact surface 705 adjacent the support member 702. The liner 704 includes a flap or pocket 706 at an upper portion for receiving a portion of the support member and at least one, and preferably two, straps 708.

Figure 9A:
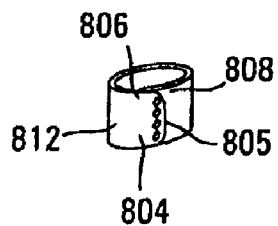
FIG. 9A shows a perspective view of a torso orthotic liner according to a sixth embodiment of the present invention.
Figure 9B:
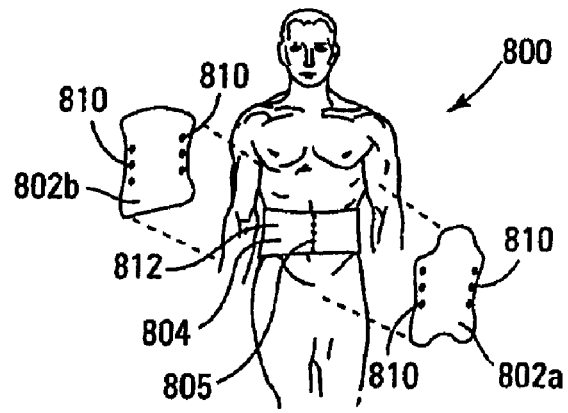
FIG. 9B shows an exploded view of a torso support member for use with the orthotic liner of FIG. 9A.

FIGS. 9A and 9B show an orthotic device 800 according to a sixth embodiment of the present invention for supporting and stabilizing the torso. The orthotic device 800 includes front and back support members 802a, 802b. The inner liner 804 is shaped to be worn about the torso and includes means 805 for securing a first end 806 to a second end 808 to form a tube shape as shown. The front and back support members 802a, 802b are secured to one another along lateral edges 810 according to any of a variety of means, including hook and loop members, hooks, laces or straps. An outer surface 812 of the liner 804 is formed of a non-slip or non-skid material as previously described. The outer surface 812 grips the front and back support members 802a, 802b and prevents migration of the support members 802a and 802b, including riding up, slipping down and rotation about the wearer's torso.

Figure 10A:
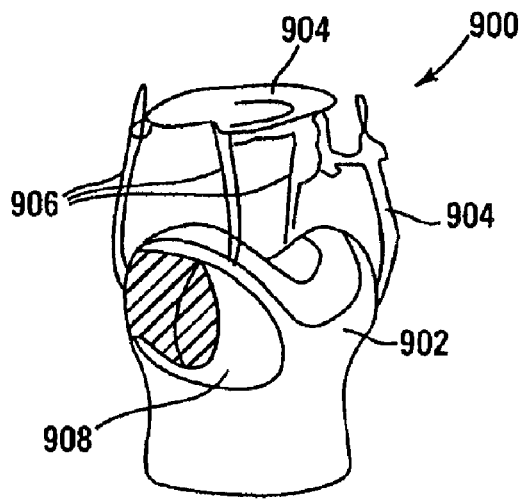
FIG. 10A shows a perspective view of a neck orthotic device including a liner according to a seventh embodiment of the present invention.
Figure 10B:
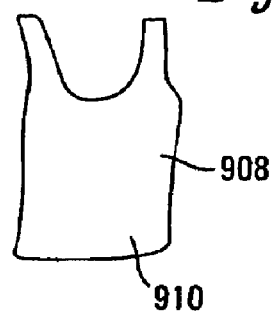
FIG. 10B shows the liner of FIG. 10A.

FIGS. 10A and 10B show an orthotic device 900 according to a seventh embodiment of the present invention for use in stabilizing the head and neck. The orthotic device 900 includes a plurality of support members, including a shoulder support 902, a head stabilizer 904, and connectors 906 extending between the shoulder support 902 and the head stabilizer 904, as well as an inner liner 908. The inner liner 908 generally resembles a tank-style shirt and is donned over the head. An outer or contact surface 910 of the liner 908 adjacent the shoulder support member 902 is formed of a non-slip or non-skid material as previously described. The outer surface 910 grips the shoulder support 902 and prevents migration of the shoulder support. An inner surface of the liner 908 may be adapted for patient comfort as previously described (not shown). Additional liners may be provided at the head stabilizer 904.

Figure 11:
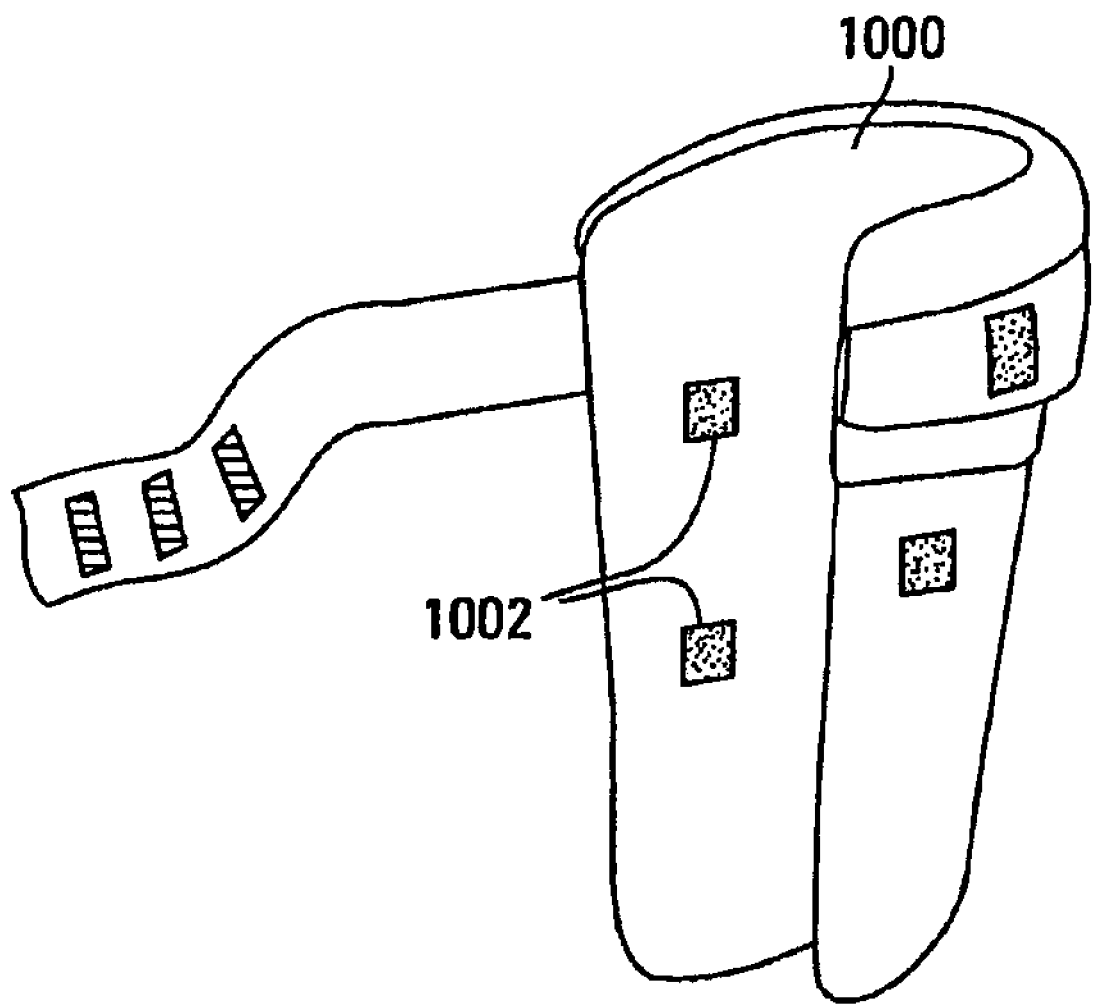
FIG. 11 shows the liner of FIG. 2 according to another embodiment of the present invention.

FIG. 11 shows a liner 1000 according to another embodiment of the present invention that is generally similar to the liner 104 shown in FIG. 2. In addition to a non-slip or non-skid outer or contact surface and any of the other features previously described, liner 1000 includes a plurality of sensors 1002. Sensors 1002 may be adapted to sense at least one of pressure, force, temperature or moisture with respect to the limb, to a support member or to a space therebetween. The output of sensors 1002 may be used by a doctor or orthotic fitter to evaluate the fit and comfort of the liner and/or the orthotic or to monitor conditions inside the orthotic device. Sensors may be incorporated in varying numbers and configurations in any of the liners and orthotic devices previously described. Liner sensors and methods of utilizing such sensor data are described in more detail in U.S. patent application 2004/0167638 published Aug. 26, 2004, which is hereby incorporated by reference herein in its entirety.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An orthotic liner for an orthotic device for supporting a portion of the body, the orthotic liner comprising:
   a body member sized and shaped to conform to at least a portion of a support member inner surface, the body member having a non-slip outer surface adjacent the support member inner surface, wherein the body member is fixed in position relative to the support member upon contact between the body member outer surface and the support member inner surface;
   a flap extending from the body member and over at least a portion of an outer surface of the support member when the body member is in the fixed position; and
   a strap having a first end attached to the body member at a first region and a second end securable to the flap such that the strap at least partially wraps around a portion of the outer surface of the support member when the body member is in the fixed position and the second end of the strap is secured to the flap.

2. The orthotic liner of claim 1, wherein the body member outer surface is disposed adjacent to a cushioning interface.

3. The orthotic liner of claim 1, wherein an inner surface of the body member is formed of a breathable material.

4. An orthotic device comprising:
a support member sized and shaped to support a portion of the body, the support member having an inner surface for receiving the portion of the body; and
a liner sized and shaped to conform to at least a portion of a support member inner surface, the liner having a non-slip outer surface adjacent the support member inner surface, wherein the liner is fixed in position relative to the support member upon contact between the liner outer surface and the support member inner surface;
a flap extending from the liner and over at least a portion of an outer surface of the support member when the liner is in the fixed position; and
a strap having a first end attached to the liner at a first region and a second end securable to the flap such that the strap at least partially wraps around a portion of the outer surface of the support member when the liner is in the fixed position and the second end of the strap is secured to the flap.

5. The orthotic device of claim 4, wherein the support member includes a foot support hingedly coupled to a calf support.

6. An orthotic device for supporting a portion of the body, the orthotic device comprising:
a support member including a foot support hingedly coupled to a calf support, the support member having an inner surface for receiving the portion of the body; and
a liner sized and shaped to conform to at least a portion of a support member inner surface, the liner having a non-slip outer surface adjacent the support member inner surface, wherein the liner is fixed in position relative to the support member upon contact between the liner outer surface and the support member inner surface;
a flap extending from the liner and over at least a portion of an outer surface of the support member when the liner is in the fixed position; and
a strap having a first end attached to the liner at a first region and a second end securable to the flap at a second region such that the strap at least partially wraps around a portion of the outer surface of the support member when the liner is in the fixed position and the second end of the strap is secured to the flap.

7. The orthotic device of claim 6, wherein an anterior portion of the liner forms a gap.

8. An orthotic device for supporting a portion of the body, comprising:
a support member having a foot support hingedly coupled to a calf support, the calf support including an inner surface and an outer surface;
a liner member positioned to conform to and contact at least a portion of the inner surface of the calf support, the liner member having a non-slip outer surface adjacent the inner surface of the calf member and an inner surface adapted to contact a calf of a user; and
a strap having a first end attached to the liner at a first region and a second end securable to the liner at a second region such that the strap at least partially wraps around a portion of the outer surface of the calf member.

9. The orthotic liner of claim 8 wherein the body member outer surface is formed of a different material than the body member inner surface.

10. The orthotic liner of claim 8 wherein the body member inner surface and the body member outer surface are separated by a cushioning material.

* * * * *

UNITED STATES PATENT AND TRADEMARK OFFICE
CERTIFICATE OF CORRECTION

PATENT NO.       : 7,625,348 B2                                    Page 1 of 1
APPLICATION NO. : 11/426073
DATED            : December 1, 2009
INVENTOR(S)      : Young et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 444 days.

Signed and Sealed this

Twenty-sixth Day of October, 2010

David J. Kappos
*Director of the United States Patent and Trademark Office*